United States Patent [19]

Shana'a

[11] Patent Number: 5,393,450
[45] Date of Patent: Feb. 28, 1995

[54] WASHING COMPOSITION CONTAINING FATTY ACID ESTERS

[75] Inventor: May Shana'a, Merseyside, Great Britain

[73] Assignee: Lever Brothers Company, Division of Conopco, Inc., New York, N.Y.

[21] Appl. No.: 148,444

[22] Filed: Nov. 8, 1993

[30] Foreign Application Priority Data

Nov. 9, 1992 [GB] United Kingdom ............... 9223439

[51] Int. Cl.⁶ .................... C11D 7/50; C11D 1/72
[52] U.S. Cl. ................... 252/170; 252/173; 252/174.23; 252/174.21; 252/549; 252/DIG. 5
[58] Field of Search ............ 252/89.1, 173, 174.23, 252/108, DIG. 5, 174.21, 170, 549

[56] References Cited

U.S. PATENT DOCUMENTS

| | | | |
|---|---|---|---|
| 4,678,606 | 7/1987 | Akhter et al. | 252/542 |
| 4,772,427 | 9/1988 | Dawson et al. | 252/559 |
| 4,898,690 | 2/1990 | Bitter et al. | 252/554 |
| 5,030,374 | 7/1991 | Tranner | 252/90 |

FOREIGN PATENT DOCUMENTS

| | | |
|---|---|---|
| 0160269 | 11/1985 | European Pat. Off. . |
| 0486074 | 5/1992 | European Pat. Off. . |
| 2650291 | 2/1991 | France . |
| 236014 | 5/1986 | Germany . |
| 92/17154 | 10/1992 | WIPO . |
| 93/09761 | 5/1993 | WIPO . |

OTHER PUBLICATIONS

Happi Household & Personal Products Industry, vol. 18, No. 2 (Feb. 1981).

*Primary Examiner*—Paul Lieberman
*Assistant Examiner*—Lorna M. Douyon
*Attorney, Agent, or Firm*—Ronald A. Koatz

[57] ABSTRACT

The present invention provides an aqueous shower-gel composition comprising: 10–30% wt of an anionic surfactant, 3–15% wt of an oily component, the ratio of said anionic surfactant to said oil being at least 1:1, 1–5% wt of a fatty acid monoglyceride polyglycol ether, and, 1–5% wt of at least one nonionic surfactant having a HLB between 5 and 10. The oily component is present at a level which provides a skin benefit. The composition has a viscosity suitable for use as a shower-gel, contains an effective level of low molecular weight moisturising oil and does not lose product structure due to the presence of this oil. Typically, the oily component is a 3–6 carbon alcohol ester of a fatty acid having at least 10 carbon atoms.

7 Claims, No Drawings

WASHING COMPOSITION CONTAINING FATTY ACID ESTERS

TECHNICAL FIELD

The present invention relates to washing compositions. More particularly, the invention relates to so-called 'shower-gel' compositions for washing the human body and which deliver oily components to the skin and/or hair.

BACKGROUND TO THE INVENTION

It is well known to use oils to deliver a skin feel benefit. For example it has been known since antiquity to add oil to bathwater so as to obtain a benefit, by deposition of a portion of the oil onto the skin. It is also known to prepare compositions which contain both one or more oils and a surfactant so as to form an emulsion on dilution with bathwater.

Over the past few decades, for reasons of economy, showers have become increasingly popular and so-called 'shower gels' have become increasingly popular as washing compositions. Shower gels generally differ from bath additives in that they have a higher viscosity, due to the presence of higher levels of thickening surfactant systems and electrolytes. The high viscosity of shower gels is necessary to prevent the composition being washed off the skin before a foam can be developed and soil can be solubilised.

It is known to include oils in shower-gel formulations, these oils have been selected from relatively high molecular weight oils such as silicone oil and relatively low molecular weight oils such as mineral oils and oily esters such as isopropyl palmitate and myristate. In the context of the present invention a low molecular weight oil is one with a molecular weight below 4000.

Isopropyl palmitate and myristate are known and used as moisturisers in skin products such as hand creams and the like. Hand creams are non-foaming, highly thickened compositions which can comprise a lamellar phase of surfactant or which employ other thickening agents incompatible with foaming surfactants.

In shower gels, only low levels of the above-mentioned low molecular weight oils have been employed, as higher levels of these oils are incompatible with the foaming surfactants generally employed.

It is believed that the levels of relatively low molecular weight, moisturising oils present in known shower-gel compositions are insufficient to achieve the desired skin-benefits.

The technical problem faced by the present invention, is therefore to provide a foaming composition having a viscosity suitable for use as a shower-gel, which contains an effective level of low molecular weight moisturising oil and which does not lose product structure due to the presence of this oil.

BRIEF DESCRIPTION OF THE INVENTION

We have determined that some or all of the above-mentioned difficulties can be overcome by formulating an oily shower gel with an anionic surfactant using a fatty acid monoglyceride polyglycol ether as a thickening surfactant in the presence of at least one of a specified class of emulsifier, namely the nonionics having a HLB of 5-10.

DETAILED DESCRIPTION OF THE INVENTION

The present invention provides an aqueous shower-gel composition comprising:
 a) 10–30% wt of an anionic surfactant,
 b) 3–15% wt of an oily component, the ratio of said anionic surfactant to said oil being at least 1:1.
 c) 1–5% wt of a fatty acid monoglyceride polyglycol ether, and,
 d) 1–5% wt of at least one nonionic surfactant having a HLB between 5 and 10.

Oily Component

The oily component is an essential element of compositions according to the present invention. The oily component is present at a level, 3–15% wt on product which provides a skin benefit. Preferred levels of oily component range from 5–10% wt on product.

One function of the oily component is believed to be that of reducing water loss from the stratum corneum. There are believed to be two mechanisms by which this can be accomplished. One is to deposit on the surface of the skin an occlusive layer which reduces the rate of evaporation. The second method is to add nonocclusive hydgroscopic substances to the stratum corneum which will retain water, and make this water available to the stratum corneum to alter its physical properties and produce a cosmetically desirable effect. Nonocclusive moisturisers also function by improving the lubricity of the skin.

Both occlusive and nonocclusive moisturisers can work in the present invention. Some examples of moisturisers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Some occlusive moisturisers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Preferably the oily component is a non-occlusive moisturiser.

Examples of non-occlusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate).

Typically, the oily component is a 3–6 carbon alcohol ester of a fatty acid having at least 10 carbon atoms.

Preferably, the alcohol is a branched chain alcohol, most preferably isopropanol. The preferred fatty acids are selected from the group comprising, myristic, palmitic and mixtures thereof.

All the above-mentioned oils have a molecular weight below 4000. It is preferred to use oils with a molecular weight below 2000, more preferably below 1000.

The most preferred moisturisers are isopropyl palmitate and isopropyl myristate.

Other examples of both types of moisturisers are disclosed in "Emollients—a Critical Evaluation," by J. Mausner, Cosmetics & Toiletries, May 1981,

Anionic Surfactant

The anionic surfactant is the foaming surfactant and is an essential component of the compositions of the present invention.

Examples of the anionic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates, sulphonated polycarboxylic acids prepared by sulphonation of the pyrolyzed product of alkaline earth metal citrates, e.g., as described in British Patent specification, 1,082,179, 8 to 22 carbon alkylsulphates, 8 to 24 carbon alkylpolyglycol-ethersulphates, -carboxylates and -phosphates (containing up to 10 moles of ethylene oxide); further examples are described in "Surface Active Agents and Detergents" (vol. I and II) by Schwartz, Ferry and Bergh.

Preferred anionic surfactants are selected from; alkyl ether sulphates, fatty acid soaps, alkyl sulphates, alkyl sulphonates, isethionic acid derivatives and mixtures thereof. One particularly preferred non-soap anionic is a $C_8$–$C_{22}$ alkyl unsubstituted isethionate. These ester may be prepared by the reaction between alkali metal isethionate and mixed aliphatic fatty acids having from 8 to 22 carbons. The most preferred anionic surfactants are the alkyl ether sulphates due to the mildness of compositions based on this component.

Preferred levels of anionic surfactant fall in the range 10–20% wt.

The anionic surfactant: oil ratio is preferably in the range 1:1 to 20:1, more preferably 1:1 to 5:1.

First Nonionic Surfactant

The nonionic surfactant, having an HLB in the range 5–10 is an emulsifier for the oily component and it's presence is essential for the performance of the invention.

Suitable nonionic surfactants include alcohol ethoxylates, having an alkyl chain length and degree of ethoxylation which exhibits an HLB in the specified range.

Preferred alcohol ethoxylates have a chain length of C10–C16 and an ethoxylation value of 3–7. The higher chain lengths, C12 and above are particularly preferred due to the low levels of free alcohol in commercially available materials.

Preferred ratios of the components are such that the ratio of the non-ionic emulsifier to the oil falls in the range 1:10 to 10:1.

In general terms ratios which comprise relatively lower levels of emulsifier form emulsions with larger drops, these are generally opaque or cloudy. These emulsions, having a ratio range of 1:10 to around 3:10 emulsifier:oil show good deposition of the oil onto skin.

Higher levels of emulsifier lead, typically in emulsifier:oil ratios above 3:10, to transparent compositions. The exact changeover point from cloudy to clear for any particular composition is dependent in part on the content of electrolyte.

Transparent compositions are preferred.

Second Nonionic Surfactant

The fatty acid monoglyceride polyglycol ether is present as a thickening surfactant and is the fourth essential component of the compositions.

Fatty acid monoglyceride polyglycol ethers are believed to have the structure:

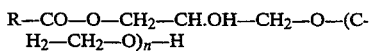

where R is a straight or branched chain alkyl group of chain length 8–16 carbons, preferably around 12 carbons, and n is 1–5, preferably around 3.

Electrolytes

Generally, electrolyte will be present in the compositions of the present invention at a level of up to about 4% wt. Suitable electrolytes are alkali metal halides, preferably sodium and potassium chlorides, other salts such as sulphates can be employed although the above-mentioned chlorides are preferred.

The presence of electrolyte, and the levels present, will influence the viscosity of the product.

Viscosity ranges for the products according to the present invention are 3000–12000, preferably 3000–7000 mPas at a shear rate of one reciprocal second, typically measured using a Haake (TM) rotary viscometer using the standard method described in the operator manual.

Minors

Compositions of the present invention may comprise an optional polymeric skin feel and mildness aid.

Polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%.

Other types of high molecular weight polymeric skin feel and skin mildness aids, such as nonionic guar gums, Merquats TM 100 and 550, made by Merck & Co, Inc.; Jaguar C-14-S made by Stein Hall; Mirapol TM A15 made by Miranol Chemical Company, Inc.; and Galactasol TM 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is Jaguar® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Particularly preferred are Jaguar TM or Polymer JR TM present at levels of 0.01–3% wt on product.

Compositions of the present invention comprise 0–10% wt of a co-surfactant, preferably an amphoteric or zwitterionic detergent. Examples of suitable co-surfactants are N-alkylamine acids, betaines, sulphobetaines and condensation products of fatty acids with protein hydrolysates. The preferred co-surfactants are betaines.

Other inessential but typical components of the compositions according to the present invention can be selected from one or more of opacifiers, preferably 0.2–2.0% wt; preservatives, preferably 0.2–2.0% wt and perfumes, preferably 0.5–2.0 wt %. Optional components include colouring agents, germicides, conditioning agents, humectants, anti-oxidants and preservatives.

Preferred compositions are stable, viscous, transparent, aqueous shower-gel composition comprising:
a) 10–15% wt of an anionic surfactant,
b) 5–10% wt of an oily component,
c) 1–5% wt of a fatty acid monoglyceride polyglycol ether,
d) 1–5% wt of at least one nonionic surfactant having a HLB between 5 and 10,
e) 1–4% wt electrolyte, and,
f) 0.01–1% of a cationic polymer.

Particularly preferred embodiments of the invention comprise:
a) 10–15% wt of an ethoxylated anionic surfactant,
b) 5–10% wt of a 3–6 carbon alcohol ester of a fatty acid having 10–20 carbon atoms,
c) 1–5% wt of a C8–C16 fatty acid monoglyceride polyglycol ether with an ethoxylation value of 1–5,
d) 1–5% wt of an alcohol ethoxylate having a chain length of C10–C16 and an ethoxylation value of 3–7,
e) 1–4% wt electrolyte, and,
f) 0.01–1% of a cationic polymer,
said composition being in the form of a clear, aqueous gel having a viscosity of 3000–7000 mPas at a shear rate of one reciprocal second, measured using a Haake rotary viscometer using the standard method.

In order that the present invention may be further understood it will be described hereafter with reference to the following examples:

EXAMPLES

The following materials are used in the examples:
SLES: Genapol ZRO (RTM ex. Hoechst) anionic surfactant.
NONI: Rewoderm LIS 75 or LIS 80 (RTM ex. Rewo), fatty acid monoglyceride polyglycol ether.
POLY: Carbopol 980/981 (RTM ex. Goodrich) a polyacryate, thickening polymer.
EMUL: Genapol UD-030 (RTM ex. Hoechst) alcohol ethoxylates have a chain length of C11, an ethoxylation value of 3 and a HLB of 8.
BRIJ: BRIJ-58 (RTM ex. Atlas) alcohol ethoxylates have a chain length of C16, an ethoxylation value of 20 and a HLB above 10.
IPP: Isopropyl palmirate (ex. Unichema).
JAG: Jaguar-C13S (ex. Mayhall), cationic polymer based on guar gum.
Salt: Sodium Chloride.
Pres: Sorbic acid (ex Hayes) and trisodium citrate (ex BDH), as preservative at an effective level.
Perl: Ethylene glycol mono-stearate (ex Albright and Wilson) as pearlescer.
Perf: Commercially available toiletry perfume.

Compositions according to the present invention and comparative examples were prepared according to the following procedure:

The oily component was combined with the nonionic surfactant emulsifier, under shear at 40° C. Water was slowly added to form an emulsion and the anionic surfactant combined with the emulsion, this method gives a fine emulsion. The salt and the thickening surfactant were added sequentially. Where EGMS was used the process was performed at a higher temperature (60° C.) and the EGMS added in the first stage. Preservative was added to the hot mixture, which was cooled before addition of the perfume, still under shear.

Stability of the compositions was assessed both at a temperature of 20° (room temperature) and 37° (body temperature) Celcius, in terms of the storage time before visible phase separation occurred. Compositions which are stable for at least three months under the conditions specified are considered to be sufficiently stable.

All figures age given in wt% on product unless otherwise specified.

Table 1 below shows examples of embodiments of the present invention. The figures given at S-20 and S-37 are the storage stabilities as mentioned above. The viscosity (visc) was measured at a shear rate of one reciprocal second and is expressed in Pascals.

TABLE 1

| COMPONENT | EXAMPLES | | | | | | | | | | |
|---|---|---|---|---|---|---|---|---|---|---|---|
| | 1 | 2 | 3 | 4 | 5 | 6 | 7 | 8 | 9 | 10 | 11 |
| SLES | 12 | 12 | 15 | 12 | 12 | 13 | 13 | 13 | 13 | 13 | 13 |
| NONI | 3 | 3 | 2 | 3.27 | 4 | 3 | 3 | 3 | 3 | 3.75 | 3 |
| EMUL | 3 | 3 | 3 | 2 | 2 | 3 | 3 | 4 | 3 | 2 | 2 |
| IPP | 5 | 5 | 10 | 10 | 5 | 10 | 10 | 10 | 10 | 10 | 10 |
| JAG | — | 0.1 | 0.1 | 0.1 | 0.1 | — | — | — | — | — | — |
| Salt | 3 | 3 | 2 | 3 | 3 | 2 | 3 | 3 | 1.3 | 3 | 4 |
| Pres | 0.7 | 0.7 | 0.7 | 0.7 | 0.7 | 0.7 | 0.7 | 0.7 | 0.7 | — | — |
| Perl | — | — | — | — | — | 2 | 2 | 2 | 2 | 2 | 2 |
| Perf | 1 | 1 | 1 | 1 | 1 | 1 | 1 | 1 | 1 | 1 | 1 |
| water | To 100% | | | | | | | | | | |
| visc | — | — | — | — | — | 9.2 | 10 | 11.4 | 6.76 | 6.02 | 11.39 |
| S-20 | >6 | 3 | 6 | 6 | 5 | >3 | >3 | >3 | >3 | >3 | >3 |
| S-37 | — | — | — | — | — | >3 | >3 | >3 | >3 | >3 | >3 |

Certain of the compositions (for example formulation 3) given in the above-mentioned table are transparent.

Table 2 below shows comparative examples which did not exhibit the required stability. The figures given at S-20 and S-37 are the storage stabilities as mentioned above. The viscosity ('visc') was measured at a shear rate of one reciprocal second and is expressed in Pascals. The stability periods are indicated in hours or days. In some circumstances the products became unstable after a few hours while the experimenter was absent and the approximation 'hrs' has been used. In some examples, a polymer has been used as an alternative to the thickening surfactant. In other examples, a nonionic with a different HLB level has been used instead of the emulsifying nonionic.

TABLE 2

| COMPONENT | COMPARATIVE EXAMPLES | | | | | | | | | |
|---|---|---|---|---|---|---|---|---|---|---|
| | 1A | 2A | 3A | 4A | 5A | 8A | 9A | 10A | 11A | 12A |
| SLES | 13 | 13 | 13 | 13 | 13 | 13 | 13 | 13 | 13 | 12 |
| NONI | 2 | 2 | 2 | 1.5 | 3 | 3 | 3 | 3 | 2 | 3 |
| POLY | — | — | — | — | — | — | — | — | — | 0.2 |
| EMUL | 2 | 2 | 2 | 2.5 | 2 | 4 | 3 | — | — | 5 |
| BRIJ | — | — | — | — | — | — | — | 2 | 2 | — |
| IPP | 10 | 10 | 10 | 10 | 10 | 10 | 10 | 10 | 10 | 5 |
| Salt | 2 | 2 | 3 | 2 | 2 | 1 | 1 | 4 | 4 | 3 |
| Pres | 0.7 | 0.7 | 0.7 | 0.7 | 0.7 | 0.7 | 0.7 | 0.7 | 0.7 | 0.7 |
| Perl | 1 | 2 | 2 | 2 | 2 | 2 | 2 | 2 | 2 | 2 |
| Perf | 1 | 1 | 1 | 1 | 1 | 1 | 1 | 1 | 1 | 1 |
| water | to 100% | | | | | | | | | |
| visc | — | — | — | — | 4.17 | — | — | — | — | — |
| S-20 | hrs | hrs | 5h | 12h | 8d | 6d | 6d | 6d | 6d | 14d |
| S-37 | 0 | 0 | 2h | 2h | 8h | hrs | hrs | hrs | hrs | 0 |

I claim:

1. Aqueous shower-gel composition comprising:
   a) 10–30% wt. of an anionic surfactant,
   b) 5–10% wt. of an oily component which is a 3–6 carbon alcohol ester of a fatty acid having at least 10 carbon atoms, the ratio of said anionic surfactant to said oil being at least 1:1,
   c) 1–5% wt. of a fatty acid monoglyceride polyglycol ether, and,
   d) 1–5% wt. of at least one nonionic surfactant having a HLB between 5 and 10.

2. Composition according to claim 1 wherein the oily component (b) has a molecular weight below 4000.

3. Composition according to claim 1 further comprising 1–4% wt electrolyte selected from alkali metal halides.

4. Composition according to claim 1 wherein the ratio of components (d):(b) falls in the range 1:10 to 10:1.

5. Composition according to claim 1 wherein the ratio of components (a):(b) falls in the range 1:1 to 20:1.

6. A Composition according to claim 1 having a viscosity of 3000–7000 Mpas at a shear rate of one reciprocal second, measured using a Haake rotary viscometer using the standard method.

7. Composition according to claim 1 comprising:
   a) 10–15% wt of an ethoxylated anionic surfactant,
   b) 5–10% wt of a 3–6 carbon alcohol ester of a fatty acid having 10–20 carbon atoms,
   c) 1–5% wt of a C8–C16 fatty acid monoglyceride polyglycol ether with an ethoxylation value of 1–5,
   d) 1–5% wt of an alcohol ethoxylate having a chain length of C10–C16 and an ethoxylation value of 3–7,
   e) 1–4% wt electrolyte, and,
   f) 0.01–1% wt of a cationic polymer,
said composition being in the form of a clear, aqueous gel having a viscosity of 3000–7000 Mpas at a shear rate of one reciprocal second, measured using a Haake rotary viscometer using the standard method.

* * * * *